(12) United States Patent
Adolfsson et al.

(10) Patent No.: US 7,798,975 B2
(45) Date of Patent: Sep. 21, 2010

(54) SENSOR DEVICE AND METHOD

(76) Inventors: Rune Adolfsson, Stackvagen 4, 432 54 Varberg (SE); Lennart Eliasson, Marsavagen 9, 430 10 Tvaaker (SE)

( * ) Notice: Subject to any disclaimer, the term of this patent is extended or adjusted under 35 U.S.C. 154(b) by 1596 days.

(21) Appl. No.: 10/527,080

(22) PCT Filed: Sep. 8, 2003

(86) PCT No.: PCT/SE03/01403

§ 371 (c)(1),
(2), (4) Date: Mar. 9, 2005

(87) PCT Pub. No.: WO2004/024000

PCT Pub. Date: Mar. 25, 2004

(65) Prior Publication Data

US 2006/0074339 A1    Apr. 6, 2006

Related U.S. Application Data

(60) Provisional application No. 60/319,550, filed on Sep. 15, 2002.

(51) Int. Cl.
*A61B 5/00* (2006.01)
*A61B 18/18* (2006.01)
*A61F 7/00* (2006.01)
*A61F 7/12* (2006.01)
*F25B 21/02* (2006.01)

(52) U.S. Cl. .................. 600/555; 606/20; 607/96; 62/3.2

(58) Field of Classification Search .............. 600/555; 606/20–28, 30–31; 607/96, 114; 62/3.2
See application file for complete search history.

(56) References Cited

U.S. PATENT DOCUMENTS

| | | | | | |
|---|---|---|---|---|---|
| 4,308,013 | A | * | 12/1981 | Major | 433/32 |
| 5,007,433 | A | * | 4/1991 | Hermsdorffer et al. | 600/555 |
| 5,097,828 | A | * | 3/1992 | Deutsch | 607/104 |
| 5,191,896 | A | * | 3/1993 | Gafni et al. | 600/555 |
| 5,830,208 | A | * | 11/1998 | Muller | 606/9 |
| 6,023,932 | A | * | 2/2000 | Johnston | 62/3.5 |
| 6,196,839 | B1 | * | 3/2001 | Ross | 433/3 |
| 6,679,908 | B2 | * | 1/2004 | Shimizu | 607/109 |
| 7,037,326 | B2 | * | 5/2006 | Lee | 607/108 |
| 2002/0082668 | A1 | * | 6/2002 | Ingman | 607/98 |

* cited by examiner

*Primary Examiner*—Max Hindenburg
*Assistant Examiner*—H. Q. Nguyen
(74) *Attorney, Agent, or Firm*—Fasth Law Offices; Rolf Fasth

(57) ABSTRACT

The sensor device has a housing. The housing is made of a material having a first high heat-conductivity index. A holder is attached to the housing and made of a material with a second low heat-conductivity index that is substantially lower than the first high heat conductivity index. The holder holds a peltier element and is connected to a power source so that the element has a cooled layer and a heated layer. A rotatable roller is in operative engagement with the layer so that the layer cools the roller. The roller may be rolled on the skin of the patient to determine the scope and effect of anesthetic treatment.

11 Claims, 3 Drawing Sheets

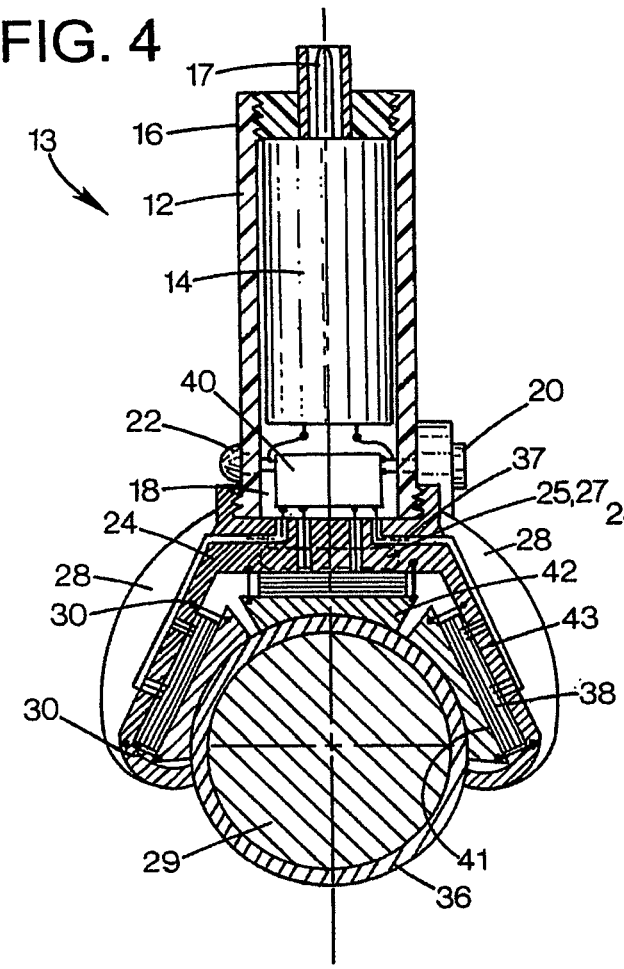

SENSOR DEVICE AND METHOD

PRIOR APPLICATION

This application is a U.S. national phase application based on International Application No. PCT/SE03/01403, filed 8 Sep. 2003, claiming priority from U.S. Provisional Patent Application Ser. No. 60/319,550, filed 15 Sep. 2002.

TECHNICAL FIELD

The present invention relates to a cooled sensor device and a method of using the device.

BACKGROUND AND SUMMARY OF THE INVENTION

Physicians/surgeons and other medical professionals often need to administer anesthetics before conducting surgery and other operations. However, it is sometimes difficult to know how effective the anesthetic drugs are and the size of the area affected. For example, when administering anesthetics to the spine it is often important to determine how high up on the spine the anesthetics have traveled. Some medical professionals test this by applying ice cubes or cold rubber alcohol to skin along the spine and the patient is asked whether the ice can be felt or not. This method is messy and unreliable.

It is also necessary for the medical professional to repeatedly go between a freezer and the patient since the ice melts at room temperature. Other professionals pinch the patient with a tool or use needles. These methods are sometimes not comfortable for the patient and not so reliable as they influence other nerve centers also. Cold gas spray device have also been used but they are uneconomic, smell bad and are not good for the environment. There is a need for a more reliable and efficient method of determining how much of the area anaesthetized is affected by the anesthetics.

The present invention solves the above-outlined problems. Firstly, the present invention has an even low surface temperature device that holds the temperature constant by a constant power supply. Secondly, the surface temperature can be held, for example, at about −5 down to −20 C depending on the power used. This is more effective than melting ice at about 0 C. Thus, the present invention is a more effective and reliable method and suitable as a standard method for testing.

More particularly, the sensor device of the present invention has a housing with a flanged section that has a threaded outer section. The flanged section is made of a material that has a high heat conductivity index.

A holder or nut is attached to the outer section and made of a material with a low heat conductivity index that is substantially lower than the first high heat conductivity index. The holder holds a peltier element is held to the outer section. The peltier element is connected to a power source so that the element has a cooled outer layer and a heated inner layer. The inner layer is in contact with the section and the outer layer may be applied on to the skin of the patient to determine the scope and effect of anesthetic treatment.

BRIEF DESCRIPTION OF THE DRAWINGS

FIG. 4 is a cross-sectional side view of a third embodiment of the sensor device of the present invention;

FIG. 5 is a cross-sectional side view of the sensor device along line 5-5 of FIG. 4; and FIG. 6 is a detailed of the curved peltier element of the sensor device of the present invention.

DETAILED DESCRIPTION

Figure 1:
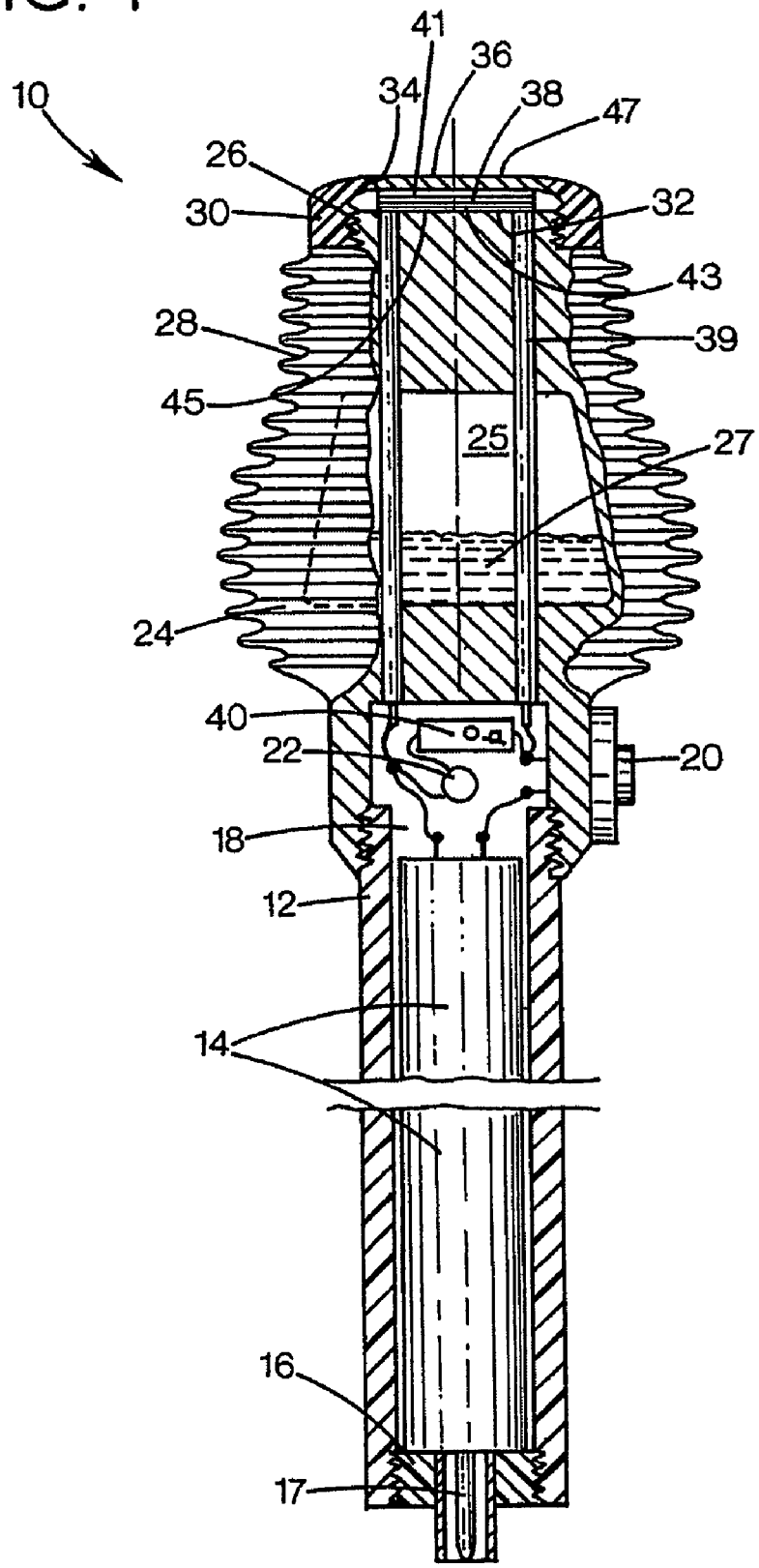
FIG. 1 is a cross-sectional side view of a first embodiment of the sensor device of the present invention.

With reference to FIG. 1, a first embodiment of the elongate sensor device 10 is shown that may be used for sensing nerve reactions of a patient by using a cold element, as explained below. The cooling element may hold a constant temperature of about −5 to −15 C or any other suitable temperature range. Only a small cooling power is required and it is often sufficient to use one peltier element. However, even lower temperatures can be accomplished by applying two peltier elements on top of each other.

The device 10 is useful for determining the area affected by, for example, anesthesia on the body of the patient. The device 10 has an elongate housing 12 that may contain a power source 14, such as batteries, held in place by a removable lid 16. A coupling 17 is arranged in the lid 16 and the coupling 17 is suitable for connecting a battery charger to the battery. A mid-portion 18 of the housing 12 has a switch 20 for turning on and off the device 10. The housing 12 may also have a light emission diode 22 that indicates whether the device 10 is turned on or not. The device 10 also has an enlarged cooling segment 24 that terminates at a threaded outer end 26. The segment 24 may contain flanges or segments to maximize a surface area 28 of the segment 24. The segment 24 may be made of an extruded aluminum or any other suitable material with a high heat-conductivity index.

The segment 24 may also be hollow and contain a volume of a material or substance 27, e.g. cooling liquid or water that has a higher thermal capacity than the material in segment 24. In this way, more heat can be absorbed during a limited time with very limited temperature increase in segment 24, especially when the ambient temperature is high and the cooling effect in the flanges 28 is lower. This is an advantage when the device 10 is used intermittently and the ambient air temperature is high that may result in a lower cooling effect from the flanges 28.

A plastic nut or holder 30 may be removably attached to a threaded end 26 of the segment 24. The holder 30 may be made of any material with a low heat-conductivity such as glass-fiber composites or plastics. The nut 30 may have a slanted inner diameter 34 to hold a cover plate 36 and a peltier element 38 against the threaded end 32. The plate 36 may be used to protect the element 38 from damage such as scratches, corrosion and wear during use and cleaning of the device 10.

The peltier element 38 is electrically connected, via wires 39, to an electrical circuit 40 that is turn is powered by the power source 14. The element 38 may have a plurality of layers and when the element 38 is electrically connected the element 38 makes a top layer 41 substantially cooler than a bottom layer 43. For example, the layer 41 may have a temperature range of −5 to −15 C while the opposite bottom layer 43 may have a temperature of +30 to +50 C depending on the power applied to the peltier element 38. In a way, the element 38 is opposite to that of a conventional thermo-element.

One important function of the solid segment 24 is to lead away the heat generated in the bottom layer 43 because an upper surface 45 of the end 26 of the segment 24 is, preferably, in direct contact with the layer 43.

Because the segment 24 has a large surface area 28 and is made of a material with high heat conductivity, the segment 24 may efficiently lead away the heat generated by the element 38 so as to increase the efficiency of the element 38. By maintaining the temperature of the layer 43 at about +35 C, it is possible to operate the element 38 at half the full effect so that the temperature difference between the cool side and the warm side is about 35-45 degrees. When operated at a full power, the temperature difference between the cooled layer 41 and the heated layer 43 may be as high as 78 C or higher. The use of the segment 24 thus saves on the energy consumption of the device 10.

In operation, the user may turn on the device 10 by switching on the switch 20. The current runs through the element 38 so that a substantial temperature difference is created between the layer 41 and the layer 43 and so that the layer 41 becomes very cold. Since the element 36 has a relatively high conductivity, an upper surface 47 of the element 36 also becomes cold. The surface 47 is applied to the patient who has been treated with anesthesia, or any other treatment, to determine if the patient can feel the cold surface 47 that is applied directly on the skin of the patient. When the effect of the anesthesia has been determined, the medical professional may turn off the device 10 by switching the switch 20 to the off mode. An automatic switch-off after a suitable time can be arranged in the switch function 20 in order to save the batteries.

As indicated above, because the segment 24 is solid and has a large surface area 28 it may be used to cool off the heated layer 43 of the element 38. The heat from the layer 43 is led into the segment 24 via the surface 45. In this way, the surface 41 may be maintained at a low temperature while keeping the temperature difference between the layers 41, 43, and energy consumption of the device 10, the same. It is important that the holder 30 is made of a material with low heat conductivity so that no heat is transferred from the layer 43 to the cooled layer 41 and the protective sheet 36.

Figure 3:
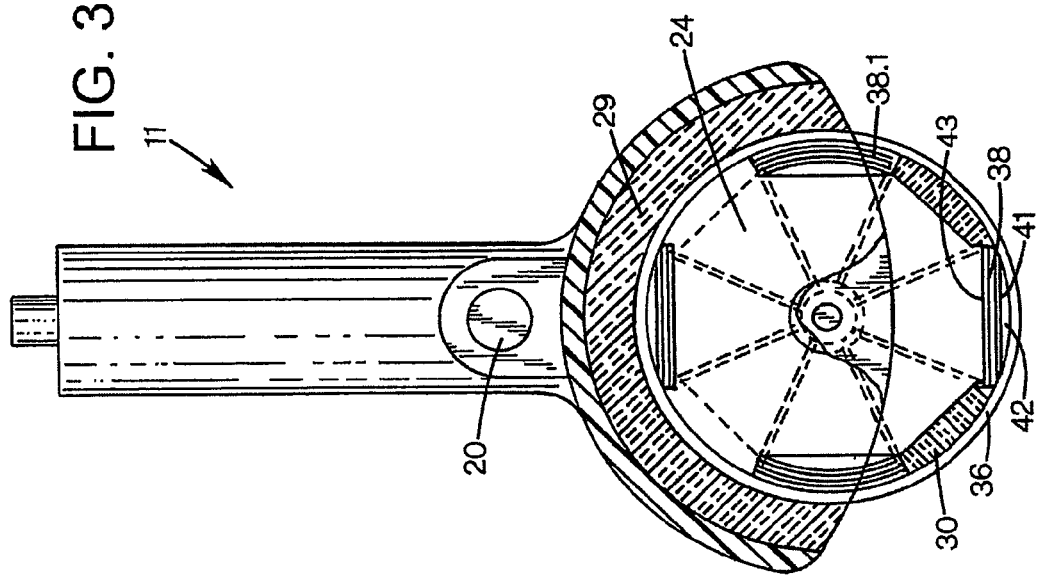
FIG. 3 is a side view of the sensor device along line 3-3 of FIG. 2.
Figure 2:
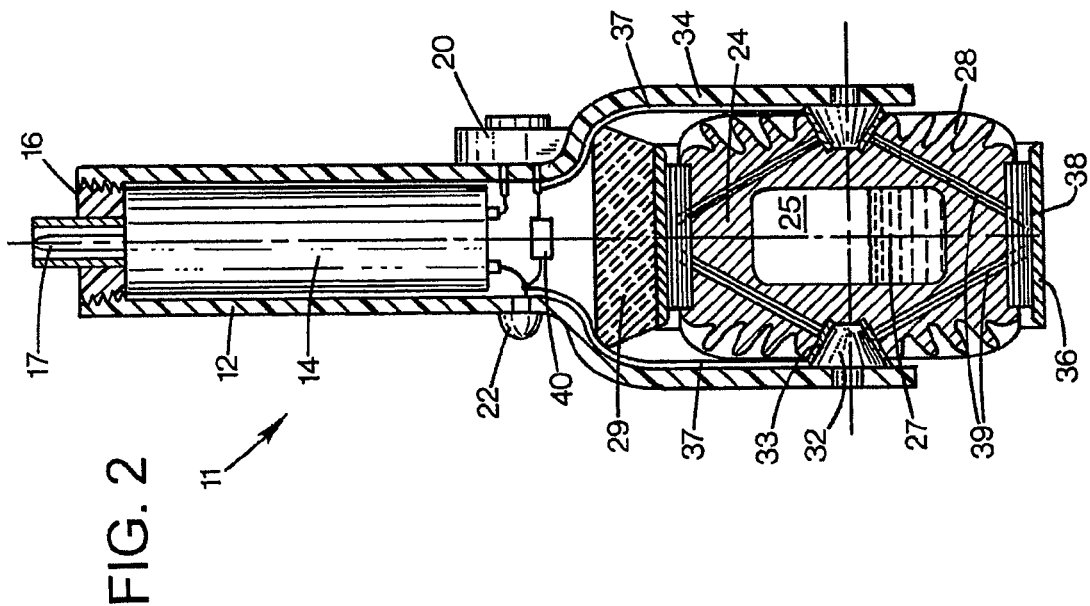
FIG. 2 is a cross-sectional side view of a second embodiment of the sensor device of the present invention.

FIGS. 2-3 are views of a device 11 with a roller 24 made of a material with a high heat conductivity that is cooled by built in peltier elements 38 and 38.1. In the roller 24 is assembled a number of peltier elements with the warm side 43 facing against the inner of the roller and the cold side 41 facing against circular segments 42 on the outside, which are built into a circular ring 36, aimed at rolling on the skin of a patient for testing the anesthetic effects. Preferably, both the ring 36 and the segments 41 are made of material with high heat conductivity.

The roller 24, which can be rotated in bearings 32, can be connected by electrical contact slide rings 33 to a power source such as the battery 14 in the handle 12, via connecting wires 37 in the handle and wires 39 in the roller to the peltier elements 38 in the roller 24.

The upper part of the roller ring 36 directed from the lower area aimed at contacting to the skin of the patient, is heat isolated by applying an isolation material 29 between the ring 36 and an inside of the handle 12 and handle arms 34 Between the peltier elements 38, heat isolation 30 can be arranged between the roller 24 and the ring 36. The wires 37 from the peltier elements 38 can be connected via an electrical system 40 to a switch 20, a diode light 22 and to the power source 14.

At the end of the handle 12, which preferably can be made of electrically isolated material, such as plastics, is a lid 16 disposed in order to close in the battery and a coupling 17 suitable for connecting the rechargeable batteries 14 to an external battery charger. The peltier elements can be connected in parallel in order to get the same voltage and power from the battery 14.

By using peltier elements, such as the peltier elements 38.1, with a curved radius that corresponds to the inner diameter of the ring 36, improved heat conduction and even distributed temperature may be achieved by eliminating the segment 42. The cooling of the roller 24 is reached by cooling flanges 28 arranged on the sides of the roller, increasing the surface to the ambient air and also getting better heat transmission by higher air speed when the roller is rotated.

By introducing a volume 25 in the roller 24 and fill it with a material with higher thermal capacity 27, than the material of the roller 24, more heat from the peltier elements can be absorbed with limited temperature increase during a limited time. This is an advantage when the device 11 is used intermittently and the ambient air temperature is high, resulting in lower cooling effect from the flanges 28.

FIGS. 4-5 are views of a device 13 with a roller 36 made of a material with high heat conductivity that is cooled by the external peltier elements 38.1 that are in contact with the roller surface via segments 42. In the housing 24 a number of peltier elements 38.1 are assembled with the warm side 43 facing outwardly against the housing 24. The cold side 41 is facing against circular segments 42 on the inside against the roller circular ring 36, aimed at rolling on the skin of the patient for testing the anesthetic and other effects. Both the ring 36 and the segments 42 may be made of material with high heat conductivity so that they can be quickly and effectively cooled by the peltier elements 38.1.

The roller 36 can be rotated in bearings, by sliding against the circular segments 42 assembled to the housing 24 by holders 30 and also holding the peltier elements 38.1 in place against the housing 24. The roller 36 with an inside insulation material 29 is cooled by the contact with the cold circular segments 42.

The peltier elements 38.1 are connected to the battery 14 in the handle 12 via an electrical system 40 by connect wires 37 in the handle and housing 24. The electrical system 40 in the mid-portion 18 of the housing 12 has a switch 20 for turning on and off the device 13. The housing 12 may also have a light emission diode 22 that indicates whether the device 13 is turned on or not. An automatic switch-off after a suitable time can be arranged in the switch function 20 in order to save the batteries.

At the end of the handle 12, which preferably can be made of electrically insulated material, such as plastic, is a lid 16 in order to close in the battery and a coupling 17 suitable for connecting the rechargeable batteries 14 to an external battery charger. The peltier elements can be connected in parallel in order to get the same voltage and power from the battery 14.

By using peltier elements 38.1 with a curved radius that corresponds to the outer radius of the bearing segment 42, improved heat conduction and even distributed temperature are accomplished. The cooling of the housing 24 may be achieved by the cooling flanges 28 disposed on the sides of the housing to increase the surface to the ambient air that results in increased cooling effect. By introducing a volume 25 in the housing 24 and fill it with a material 27 with higher thermal capacity than the housing material, more heat from the peltier elements can be absorbed with limited temperature increase in the housing 24 during a limited time. This is an advantage when the device 13 is used intermittently and the ambient air temperature is high resulting in lower cooling effect from the flanges 28.

FIG. 6 is detailed view that shows the curved peltier element 38.1 and the surfaces 43 and 41 on each side of the element 38.1. The roller 36 is disposed radially inside the element 38.1 so that it is cooled by the surface 41. In this way, the roller 36, which is cooled by the peltier elements 38.1, may be rolled on the skin of the patient to be tested.

While the present invention has been described in accordance with preferred compositions and embodiments, it is to be understood that certain substitutions and alterations may be made thereto without departing from the spirit and scope of the following claims.

The invention claimed is:

1. A hand-held sensor device applied to the skin of a patient, comprising:
   a roller which rotates about an axis, the roller being in operative engagement with a housing;
   a peltier element disposed inside the roller and having a cooled surface and a heated surface, the peltier element being connected to a power source to obtain a temperature difference between the cooled surface and the heated surface thereof, the cooled surface being cooled by the peltier element and an inner surface being heated by the peltier element and directed in a direction that is opposite the direction of the cooled surface, the cooled surface of the peltier element being in operative engagement with an inside surface of the roller to cool the roller, the roller which is cooled by the cooled surface of the peltier element being applied to the skin of the patient.

2. The sensor device according to claim 1 wherein heat is led away from the heated surface and the surface is in contact with the housing that has a high heat conductivity and formed with an area of flanges in order to increase heat transfer to another medium that is in contact with the flanges.

3. The sensor device according to claim 1 wherein a segment is in operative thermal contact with a volume containing another material that has high thermal capacity and stores heat from the inner surface.

4. The sensor device according to claim 1 wherein the peltier element is held against the housing by a holder made of a material with low heat conductivity.

5. The sensor device according to claim 1 wherein a cover plate, in contact with the peltier element, bears against a surface of the roller.

6. The sensor device according to claim 5 wherein the peltier element is in operative engagement with the cylindrical outer surface of the roller.

7. The sensor device according to claim 1 wherein the roller is rotatably attached to the housing and is made of a material with high heat conductivity.

8. The sensor device according to claim 6 wherein the roller is in contact with an isolation material that is cooled by the peltier element.

9. A hand-held sensor device applied to the skin of a patient, comprising:
   a peltier element held by a holder attached to an outer end of a housing, the housing having an enlarged cooling segment with outwardly protruding flanges that completely surrounds the peltier element, the enlarged cooling segment being made of a material with a high heat conductivity to increase heat transfer, the enlarged cooling segment disposed outside of the housing;
   the peltier element being in contact with the housing and disposed on the outer end of the housing;
   the peltier element having a cooled surface and a heated surface, the peltier element being connected to a power source to obtain a temperature difference between the cooled surface and the heated surface thereof, the cooled surface being cooled by the peltier element and an inner surface being heated by the peltier element and directed in a direction that is opposite the direction of the cooled surface;
   the cooled surface providing a cooled testing surface, the heated surface being in contact with the enlarged cooling segment of the housing that has a high heat conductivity for effectively transferring heat from the heated surface to another medium for absorbing heat, the medium contained within a cavity of the enlarged cooling segment, the medium is in direct contact with the outwardly protruding flanges of the enlarged cooling segment;
   the holder being made from a material with a low heat conductivity, that is lower than the high heat conductivity of the enlarged cooling segment of the housing, to avoid heat transfer between the cooled surface and the heated surface, the cooled testing surface being applied to the skin of the patient.

10. The sensor device according to claim 9 wherein the sensor device has a cover plate held by the holder.

11. The sensor device according to claim 9 wherein the housing has a cavity defined therein, the cavity contains a material that has a high thermal capacity higher than a thermal capacity of the housing for storing heat from the inner surface.

* * * * *